(12) United States Patent
Tihon (10) Patent No.: US 10,792,140 B2
(45) Date of Patent: Oct. 6, 2020

(54) PARTIAL CUFF

(71) Applicant: Claude Tihon, Eden Prairie, MN (US)

(72) Inventor: Claude Tihon, Eden Prairie, MN (US)

( * ) Notice: Subject to any disclaimer, the term of this patent is extended or adjusted under 35 U.S.C. 154(b) by 70 days.

(21) Appl. No.: 15/968,372

(22) Filed: May 1, 2018

(65) Prior Publication Data

US 2018/0243065 A1     Aug. 30, 2018

Related U.S. Application Data

(63) Continuation of application No. 12/122,079, filed on May 16, 2008, now Pat. No. 9,956,067.

(60) Provisional application No. 61/011,750, filed on Jan. 22, 2008, provisional application No. 60/958,420, filed on Jul. 6, 2007.

(51) Int. Cl.
| | |
|---|---|
| *A61F 2/00* | (2006.01) |
| *A61B 17/28* | (2006.01) |
| *A61B 17/12* | (2006.01) |
| *A61F 2/06* | (2013.01) |
| *A61F 2/04* | (2013.01) |
| *A61F 2/30* | (2006.01) |

(52) U.S. Cl.
CPC .......... *A61F 2/0036* (2013.01); *A61B 17/282* (2013.01); *A61F 2/004* (2013.01); *A61B 17/12* (2013.01); *A61F 2/0063* (2013.01); *A61F 2/06* (2013.01); *A61F 2002/044* (2013.01); *A61F 2002/30077* (2013.01); *A61F 2210/0066* (2013.01)

(58) Field of Classification Search
CPC . A61B 17/12; A61B 17/282; A61F 2002/044; A61F 2002/30077; A61F 2210/0066; A61F 2/0036; A61F 2/004; A61F 2/0063; A61F 2/06
See application file for complete search history.

(56) References Cited

U.S. PATENT DOCUMENTS

| | | |
|---|---|---|
| 3,726,279 A | 4/1973 | Barefoot et al. |
| 3,863,622 A | 2/1975 | Buuck |
| 4,222,377 A | 9/1980 | Burton |
| 4,428,365 A | 1/1984 | Hakky |
| 4,634,443 A | 1/1987 | Haber |
| 4,909,785 A | 3/1990 | Burton et al. |
| 4,994,020 A | 2/1991 | Polyak |
| 5,948,191 A | 9/1999 | Solovay |
| 6,432,040 B1 | 8/2002 | Meah |
| 6,491,623 B2 | 12/2002 | Snyder et al. |
| 6,491,703 B1 | 12/2002 | Ulmsten |

(Continued)

FOREIGN PATENT DOCUMENTS

FR     2 373 272 A1     7/1978

*Primary Examiner* — Christine H Matthews
(74) *Attorney, Agent, or Firm* — Crawford Maunu PLLC (57) ABSTRACT

To increase the resistance to liquid and substance flow through a lumen of a tubular organ, a flexible apparatus is appended to an exterior wall of the tubular organ such that it only partially surrounds the tubular organ. Ultimately, tissue ingrowth through the apparatus integrates the apparatus into the wall of the tubular organ. When the apparatus is applied to tubular tissue, flow though the tubular tissue is restricted. The apparatus may also support an optional expandable component, e.g., a balloon-like element that can be selectively inflated and/or deflated to restrict the lumen of the tubular tissue by a desired degree.

20 Claims, 9 Drawing Sheets

(56) References Cited

U.S. PATENT DOCUMENTS

| | | |
|---|---|---|
| 6,612,977 B2 | 9/2003 | Staskin et al. |
| 7,083,637 B1 | 8/2006 | Tannhauser |
| 2005/0055104 A1 | 3/2005 | Amal et al. |
| 2005/0288596 A1 | 12/2005 | Eigler et al. |
| 2005/0288776 A1 | 12/2005 | Shaoulian et al. |
| 2006/0129027 A1 | 6/2006 | Catona |
| 2007/0049790 A1 | 3/2007 | Wagner et al. |
| 2007/0156158 A1* | 7/2007 | Herzberg ........... A61B 17/1146 606/152 |
| 2007/0276342 A1 | 11/2007 | Lin et al. |

* cited by examiner

PARTIAL CUFF

This application is a continuation of U.S. patent application Ser. No. 12/122,079, filed May 16, 2008, now U.S. Pat. No. 9,956,067, which claims the benefit of Provisional application Ser. No. 60/958,420, filed Jul. 6, 2007, and claims the benefit of Provisional application Ser. No. 61/011,750, filed Jan. 22, 2008, the contents of which are hereby incorporated by reference.

OVERVIEW

The invention relates generally to surgically implantable flow restrictors, and more particularly to a cuff that is attachable directly to a tubular organ for increasing the flow resistance of liquids and substances through the tubular organ.

Biological tubular organs in our body are conduits for fluids, food and wastes. For example, the urethra is the conduit for urine between the bladder and the urethral meatus and it also functions to inhibit involuntary leakage. In stress urinary incontinence, urine leaks involuntarily when the person coughs or laughs.

Stress urinary incontinence occurs most commonly in women and is managed by absorbents and by surgical interventions. Many surgeries involve the implantation of a medical device to help decrease incontinence for the patient. Among these implantable medical devices for women, urethral slings, in the form of a strip of material or tissue to support under the bladder neck or mid-urethra, and with its ends anchored in anatomical locations other than the urethra or bladder, such as the pubic synthesis, and the abdominal muscles. Such slings have been favored by many urologists and gynecologists. The sling acts as a hammock to support and to lift the sagging urethra and/or bladder neck back to a normal position. This stops the bladder neck or urethra from dropping during sudden movements to minimize urine leakage. The newer generation of slings generally is implanted in one of three approaches. It is approached from the below, Ulmsten, U.S. Pat. No. 6,491,703 (the vaginal approach); from on top, Staskin et al. U.S. Pat. No. 6,612,977 (the suprapubic approach); and from below and goes laterally to the two sides (the transobturator approach, Monarc Subfascial Hammock from American Medical Systems). All three approaches involve the use of long rods passing blindly from one anatomical site to the other, and often resulting in puncturing of the bladder and/or blood vessels. Though the transobturator approach avoids the retropubic space and does not lead to puncturing of the bladder, it suffers as the other two in that it involves anatomical structures outside of the urinary tract system and thus, typically, not familiar to urological surgeons. In addition, a precise adjustment of the sling tension for each patient is not possible. This ill adjustment results in lower than expected level of efficacy and complications including urethral erosions. Furthermore, as the sling is being anchored in anatomical structures other than the urethra, it presents complications, such as injuries to bladder, blood vessels, nerves and muscles and is contraindicated for women patients who intend to have child births in the future.

For extreme cases, an artificial urinary sphincter (AUS) is implanted for the incontinence where a band, similar to a blood-pressure cuff, fully surrounds the urethra. Fluid is made to enter the band and constantly exerts compression to the urethra to occlude the urethral lumen. The patient needs to actively pump the fluid out of the band and into a balloon reservoir implanted in the abdominal area every time the patient needs to void. The AUS is a complex system and the associated surgical procedure is major, complex and long. Buuck, in U.S. Pat. No. 3,863,622 (1975), Burton, in U.S. Pat. No. 4,222,377 (1980) and Polyak, in U.S. Pat. No. 4,994,020 (1991) described an artificial sphincter (AUS) system that is a totally occlusive device having an inflatable band completely surrounding the patient's urethra. The urethra is essentially occluded continuously and constantly until the fluid in the band is actively pumped out by the patient at the time when he or she desires to urinate. Once the fluid is pumped out the AUS band, the compression surrounding the urethra is diminished and the urethral lumen for passage of urine can then open. With the AUS, patients cannot urinate without first having to actively manipulate the device to pump the fluid out of the band and into a reservoir at a distant location to remove the urethral occlusion.

Urethra is only one of the many biological tubes in the body. Other biological tubular organs include the esophagus, stomach, colon, blood vessels and the heart. All these tubes can suffer from defects and lose their intended function in controlling flow of material and fluids within them.

Broadly speaking, the present invention comprises a cuff that only partially surrounds an anatomical tubular organ, such as the urethra. Many biological soft tissue tubes are expandable in girth to accommodate passage of material through their lumen. The muscle components in the wall of the tube provide tonicity and elasticity. For example, the stomach expands as food enters, the esophagus opens up to allow food to pass down, the lower esophageal sphincter or the cardiac sphincter opens to allow passage of food but closes to prevent regurgitation of food material and stomach acid up the esophagus, intestines expand to accommodate food material and provides peristaltic action to propagate the food material down its length, and the urethra expands to allow urine to flow through. After the material has exited, the diameter of the tubular organ again retracts to its non-expanded size. The attachment of a partial cuff, made of non-elastic or limited elasticity material, and that only partially surrounds the tubular organ, will limit the expansion of the portion of the tubular organ covered by the cuff, allowing only the non-covered portion to expand. For material to pass through this juncture with the reduced expandable wall tissue, a higher force is required to open the passage way. The reduced amount of expandable tissue at the site of the partial cuff results in a higher tissue tension that would require a higher force in order to push the same amount of material through this juncture. If the cuff has been made to completely surround the tubular organ with a closed lumen, then little or no material will be able to pass through this juncture. However, when the cuff only partially surrounds the tubular organ, the portion that is not restrained by the cuff will still be able to expand, allowing passage of material. The lesser amount of tissue allowed to expand results in either a higher pressure to open the lumen to the same size or allowing only a smaller lumen to be opened due to limits on tissue stretch, or both. The partial cuff of the current invention induces an increased tonicity to the biological tubular organ. This is one of the unique and non-obvious principles of the invention, providing a means to increase material passage resistance in a biological soft tissue tube while still maintaining the profile of the biological tube.

When used in treating stress urinary incontinence, the partial cuff of the present invention does not occlude the urethra, but only add reinforcement to maintain the urethral closure pressure. Benefits of such a partial cuff include improving continence and allowing patients to void naturally and volitionally. This augmentation of a higher urethral tonicity for closure means an increased resistance to urine flow in stress situations such as when the patient laughs and coughs. As the cuff becomes an integral portion of and moves with the urethra, its ability to provide continence is not affected by the physical position the patient happens to be in or gravity. Because the partial cuff attaches to only the urethra and is not tied to other tissues and bones, the present invention also avoids many of the possible adverse events, contraindications and pitfalls with the traditional slings. As it involves only the urinary tract anatomy, urological surgeons will have intimate knowledge of the operating field and its surgical implantation will not involve long rods passing blindly through various anatomical structures.

SUMMARY

The invention, an improved surgical device and method to treat urinary incontinence, has a cuff with a flexible base member that only partially surrounds the urethra. The partial cuff does not occlude the urethra. The cuff may, but need not, incorporate an adjustable, expandable or deflatable component that applies pressure on one side of the urethra, allowing accurate adjustment to achieve desired coaptation while allowing the patient to void naturally and normally. The similar principle applies to other biological tubular organs such as the ureter, anal sphincter, stomach, esophagus, heart, etc. Hence, the invention will also treat other conditions where a flow of material needs to be modulated in a biological tube.

The invention provides a simple, minimally invasive surgical procedure. It allows adjustments after surgery and after tissues have healed by providing positive pressure to achieve the right amount coaptation needed by the patient's condition. The invention allows natural and volitional voiding for incontinent patients.

DRAWINGS

FIG. 1b is a side elevation of the embodiment of FIG. 1a;

FIG. 3b is a side elevation of the embodiment of FIG. 3a;

DETAILED DESCRIPTION

Figure 1A:
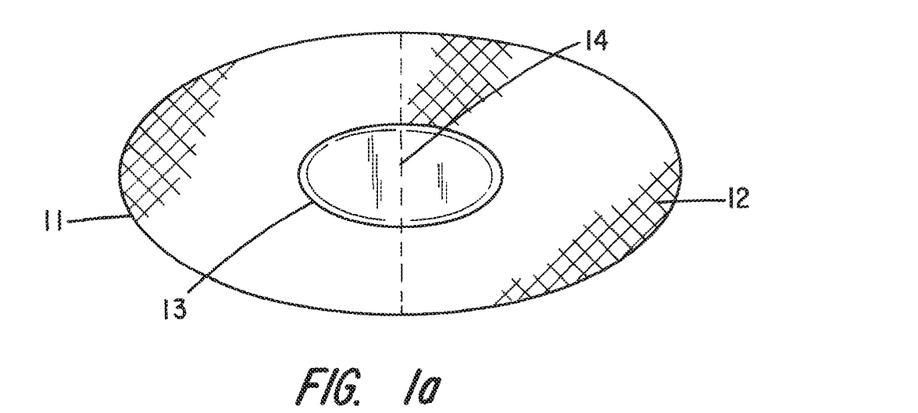
FIG. 1a is a top plan view of a first embodiment of the present invention.
Figure 1B:
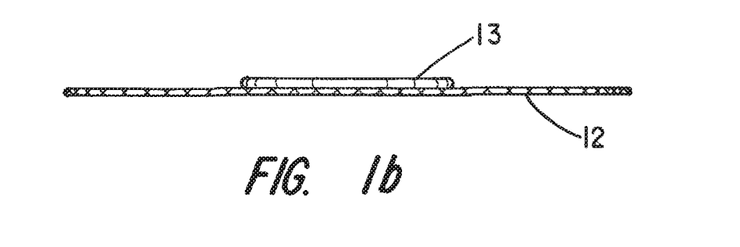

Referring to FIGS. 1a and 1b of the drawings, the partial cuff 11, comprising a first embodiment, is seen to include a flexible base member 12 that is preferably a synthetic mesh-like fabric formed from polypropylene strands like those used in surgical repair of hernias and urethral slings. That type of mesh is bio-compatible and accommodates tissue ingrowth through the interstices of the mesh material.

Without limitation, the mesh base member 12 may be generally oval or elongated in shape having a major axis measuring about 3 ems and a minor axis of about 1½ ems when the device is to be used in addressing female urinary incontinence.

In accordance with a first aspect of the invention, there is affixed to the flexible, mesh base member 12 an expandable component 13 having a predetermined shape configuration and generally centrally disposed on one major surface of the flexible base member 12. The expandable component 13 may comprise an elastomeric balloon capable of being inflated and deflated by an isotomic inflation fluid injected and removed through a suitable injection port.

Figure 2:
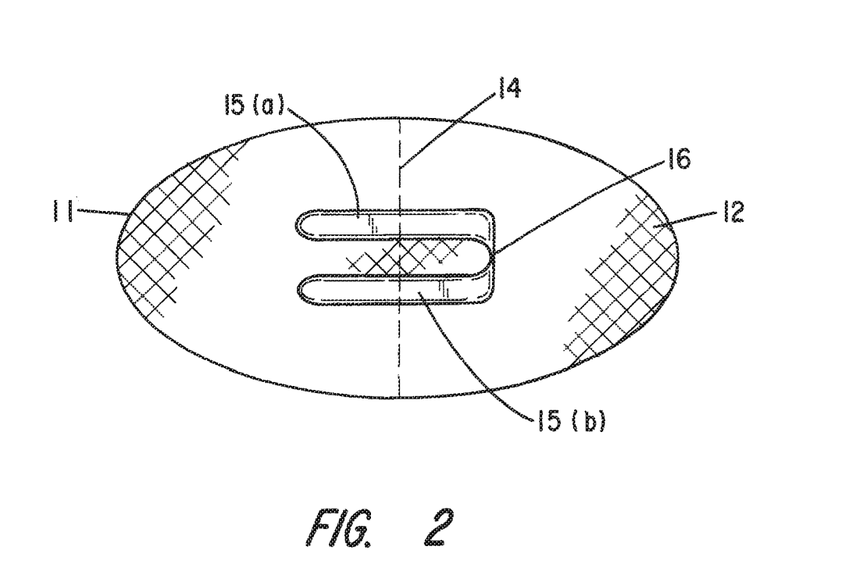
FIG. 2 is a top plan view of an alternative embodiment.

As shown in FIG. 2, the expandable component may comprise a pair of closely-spaced balloon segments 15a and 15b joined together by a tubular pathway 16. When inflated, the expandable component forms a pair of ridges that are made to press upon the urethra for increasing the flow resistance thereof.

Figure 4:
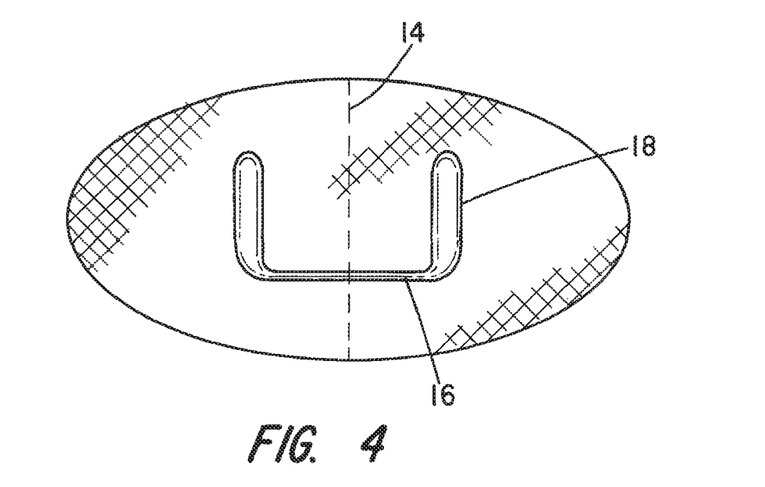
FIG. 4 is a top plan view of a further embodiment of the invention.

As shown in FIG. 4, guide line 14 and tubular pathway 16 join balloon segments 18, similar to FIG. 2 with the orientation of the tubular pathway (and balloon segments) rotated relative to the guide line.

The expandable components 13 in FIG. 1a and 15 in FIG. 2 have their length dimension generally perpendicular to a guide line 14 that is visible to a surgeon and that is useful in appropriately aligning the cuff with respect to the patient's urethra.

Figure 3A:
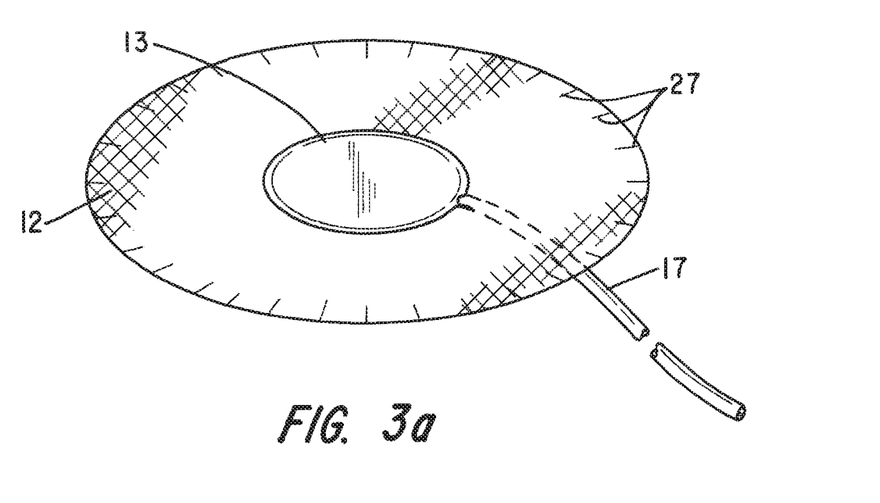
FIG. 3a shows an embodiment like that of FIG. 1 but with an inflation port feature added to it.
Figure 3B:
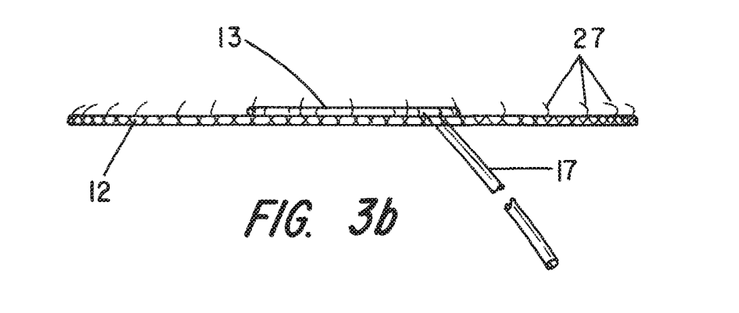

Turning next to FIG. 3a, it illustrates an inflation/deflation port 17 leading to the interior of the expandable component 13. In FIGS. 3a and 3b, the inflation port is illustrated as comprising a tube 17 that includes a purse-string suture thereabout (or a one-way valve or a self-sealing end) that can be used to seal the tube 17 once an inflation fluid, such as saline, has been fed through it to inflate the expandable component 13 to a desired state to thereby maintain the expandable component in its inflated condition.

Rather than utilizing a tube 17 as the inflation port, it is also contemplated that the expandable component 13 include a pad area of a self-sealing elastomeric material that is adapted to be punctured by a hypodermic needle affixed to an inflation syringe. The material of the inflation port is such that when the needle is removed, the opening self-seals to preclude leaking out of the inflation fluid.

An alternative method for adjusting the pressure applied is to deflate the balloon(s) that has been pre-inflated with saline prior to implantation. Once the mesh is fully integrated with the tissue, the patient will come into the clinic for this post-surgical adjustment. In this case, the physician will let out a certain amount of saline (by puncturing the balloon's inflation port with a needle) till a desired level of compression is achieved. If there are separate balloons, then the deflation process is dependent on the judgment of the physician, as he may let the saline out totally in one balloon and observe its effect. If more relief is needed, he can partially empty another balloon. The endpoint will be determined with clinical observation regarding whether the patient can void without difficulties and does not leak during Valsalva's maneuver, coughing, etc. Deflation is deemed necessary when the patient is obstructed, which means he or she has difficulty voiding. Deflating the balloon or balloons will decrease the compression on the urethra, hence the urethral lumen opening, to allow urine to pass through during natural voiding.

Another possible method of pos-surgical adjustment is via heat, such as that induced by RF energy. From the weave of the mesh, the material from which it is formed or a special material integrated with the mesh, at least a portion of the mesh can be made to shrink due to the externally applied heat, thus making the cuff tighter on the urethra. Again, this can be done in stages for fine tuning the effect once tissue ingrowth into the mesh base member has occurred.

Figures 6A, 6B:
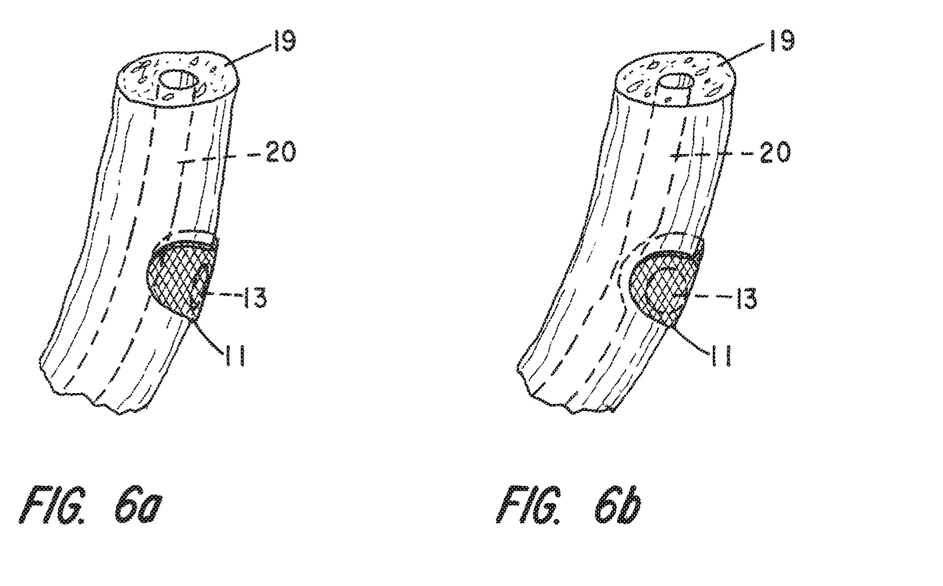
FIG. 6a is a perspective view of the cuff affixed to a tubular organ with its expandable component deflated.
FIG. 6b is a view like that of FIG. 6a but with the expandable component inflated.
Figure 7A:
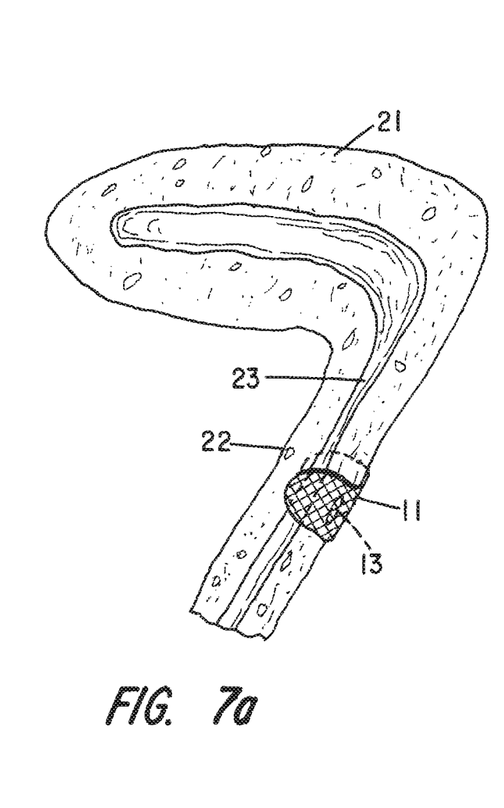
FIG. 7a shows the cuff of the present invention disposed on a tubular urethra proximate the bladder neck and with the expandable component deflated.
Figure 7B:
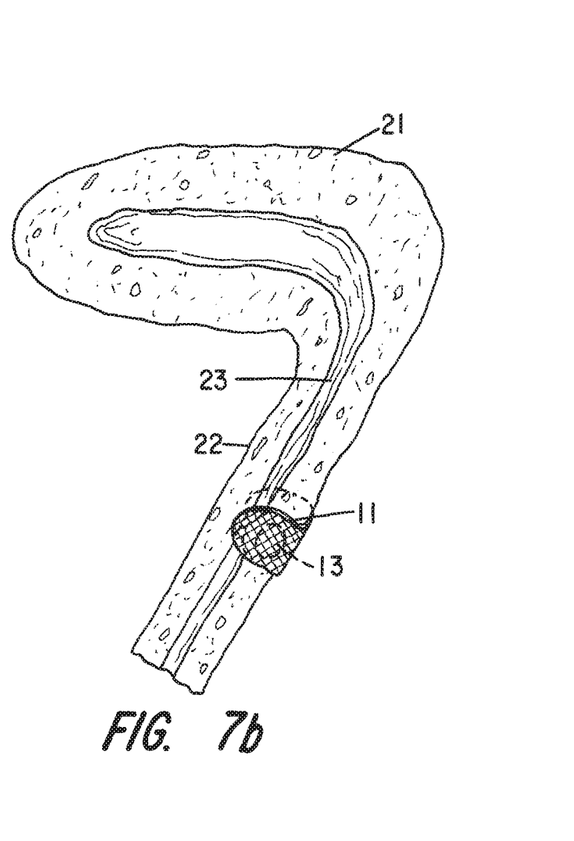
FIG. 7b is a view like that of FIG. 7a but with the expandable component inflated.

Also seen in FIG. 3b is a plurality of tissue piercing hooks 27 that is affixed to the base member 12 surrounding its periphery. When the partial cuff of the present invention is applied to a tubular organ, such as a subject's urethra, in a manner hereinafter described, the hooks are adapted to penetrate into the wall of the urethra and thereby hold the cuff in partial surrounding relation to the exterior urethral wall as shown in FIGS. 5 through 7 of the drawings.

The hooks 27 are preferably formed from a biodegradable material that will serve their purpose of adhering the cuff to the outer wall of the urethra for a time sufficient to permit tissue ingrowth in the mesh base member.

Figure 5A:
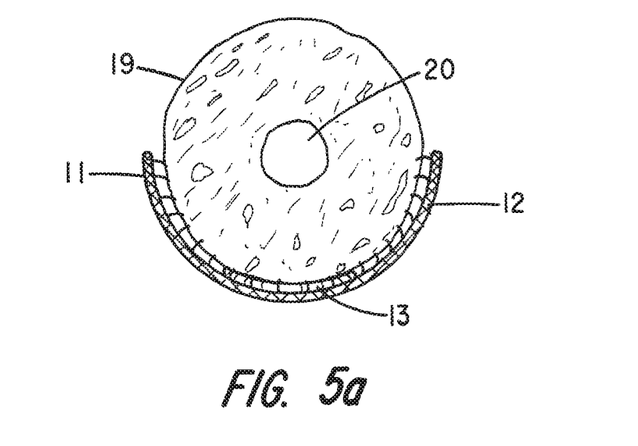
FIG. 5a is a cross-sectional view showing the preferred embodiment coapted to a tubular organ and with the inflatable component deflated.

With reference to FIG. 5a, the tubular organ 19 is shown in cross-section with the cuff 11 of the present invention surrounding approximately one-half of the circumference thereof. In this view, the expandable component 13 is shown as being deflated and with the tissue tubular lumen 20 in an open state, which it could be in an incontinent subject. If the tubular tissue represents a urethra, that would represent a patient with severe incontinence or a patient with a "stove pipe" urethra, as normally, the urethra is devoid of an open lumen at rest. A lumen only exists when urine passes through it. The base member 12 of the cuff is held in intimate contact with the exterior wall of the tubular organ, e.g. the urethra, by means of the aforementioned hooks 27 and ultimately tissue ingrowth.

Figure 5B:
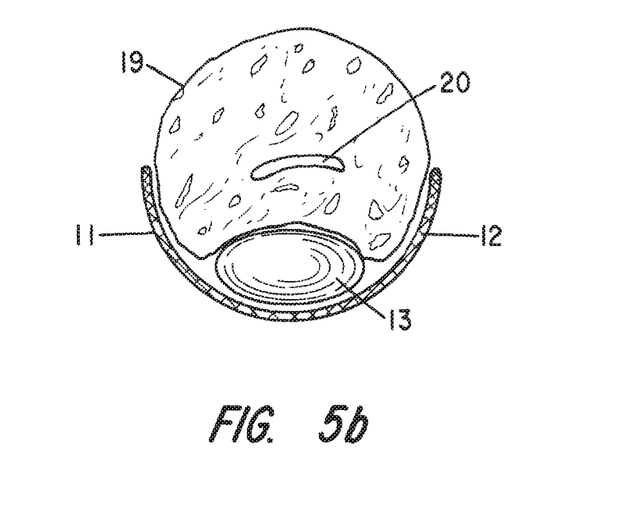
FIG. 5b shows the embodiment of the present invention coapted to a tubular organ and with the inflation component inflated.

FIG. 5b is a view like that of FIG. 5a, except with the expandable component 13 in its inflated state. As seen in this figure, the expandable component 13 pushes itself against the tubular wall to narrow or close the lumen 20 and at least increasing the resistance to fluid or other material flow therethrough.

In accordance with the present invention, by controlling the extent of inflation of the expandable component by either injecting an inflation fluid into a flaccid balloon or withdrawing fluid from a turgid balloon, the degree of closure and, hence, the resistance to fluid flow therethrough can be adjusted to the point where the tubular sphincter is capable of fully collapsing the tubular lumen and thereby keeps the subject in a dry condition such as in the case of an incontinent patient.

Those skilled in the art appreciate that the tubular organ urethra is normally without an open lumen. A lumen only exists when urine is passing through it. This means that the musculature of the urethral wall, including the sphincter muscles, are normally contracted to the keep the lumen closed, thereby preventing unwanted passage of urine, i.e., incontinence. This musculature relaxes during normal micturition. The brain sends signals to the muscles of the bladder wall, the deturusor muscle, to contract and, at the same time, to the sphincter muscles, including those muscles of the urethral wall to relax. In this way, urine is forced out of the bladder and flows down the now-relaxed urethral tube and exits the body.

Since muscles and tissues consist of mostly water, their volume is essentially not compressible. The closed urethral tube, made of tissue, can be measured to have a certain diameter. As urine creates a passageway down this tube, the diameter of this passageway, because of the non-compressible tissue mass, will be translated into an increased circumference of the urethra, exhibiting an overall increased diameter and a thinner wall. Another way to express this is that the urethral wall will be stretched to accommodate this passageway created by the urine.

The urethral wall, containing the contracted muscle, can be compared to a circular rubber band. The urine, in creating the passageway, represents a force stretching the rubber band. As an example, if the diameter of the urine passageway translates to 5 mm, this 5 mm would, therefore, be distributed into the entire cross-section of the urethra. Each segment of the urethral wall and its muscles will be stretched an apportioned length for an aggregate total of 5 mm. If one were to artificially create a situation where the cross-sectional half of the urethral wall is restricted from becoming stretched, then the other half will have to be stretched twice as much to allow the same amount of the total required expansion of 5 mm.

The contracted musculature is analogous to that of a rubber band. Stretching will require a force. If a 15 mm long rubber band is stretched to be 20 mm long, a certain amount of force will be needed. If only half of the 15 mm rubber band is allowed to stretch, then the amount of force to stretch the 5 additional mm will be greater with the 7.5 mm rubber band. Similarly, a partially restricted urethral wall will require a greater force to open than if the urethral wall were not partially surrounded by the cuff. It is this added force that is required to stretch a shortened band that forms one of the underlying principals of the present invention. If a portion of the urethra is restricted from stretching or expanding, then it will take more force to stretch the remainder of the urethra to achieve the same opening size.

As shown in FIGS. 5a, 5b, 6a and 6b, the cuff 11 restricts only a portion of the urethral wall from stretching. The unrestricted portion can still be stretched, albeit requiring more force to do so. In stress urinary incontinence, urine is forced down the urethra as the bladder is being suddenly compressed by abdominal muscle during coughing, laughing and other common daily activities. In these patients, the urethral musculature is insufficient to maintain closure, such that it lets some urine to pass through during this sudden increase in pressure on the bladder. The amount of leakage varies from patient to patient, paralleling the degree of weakness of the musculature. Analogous situations occur in fecal incontinent and acid reflux.

During normal micturition, the urethral musculature relaxes and the urethral lumen will open to allow the passage of urine freely down the path. The harder the bladder squeezes, the more urine will rush out of the bladder and down the urethra, thus a faster flow rate. This faster flow rate translates to a thicker urine stream, reflecting a wider urethral lumen.

If a restriction were to be put completely around the urethra, such that none of the urethral wall under the restriction is allowed to be stretched, then no passage lumen can be created in the urethra and no urine can flow through it. This is somewhat analogous to males with a severe case of benign prostatic hyperplasia (BPH) in that the enlarged prostate gland impinges on the urethra and the patient is in retention, or unable to void.

In the practice of the present invention, the novel and non-obvious principle of only applying a partial restriction to stretching or expansion of the urethra results in an increased resistance to flow that will benefit most of the stress urinary incontinent patients, and yet when these patients want to void, the unrestricted portion of the urethral wall can relax automatically, via normal and natural neural signaling, allowing urine to flow through as any normal micturition.

FIG. 7a is a sagittal view taken laterally through the bladder, bladder neck and urethra of a woman. Here, the partial cuff 11 of the present invention is adhered to the urethra at a location proximal to the urinary sphincter. Again, the cuff 11 is shown as only partially surrounding the urethra 22 and when the inflatable component 13 is in its deflated condition (FIG. 7a), the lumen 23 is unrestricted. By injecting a suitable inflation fluid into the interior of the expandable component or balloon 13, the urethral wall is displaced in a direction to at least partially occlude and increase the resistance to flow of the lumen 23. In accordance with the invention, however, the expandable component 13 is only expanded to the point where, at rest, urine flow through the urethra is blocked. However, when the signals from the brain result in contraction of the bladder wall, the resulting increase in fluid pressure will allow the urethra muscles to relax and expand sufficiently so that the lumen will open and normal voiding may take place.

In order to apply the cuff of the present invention to the urethral wall, a special tool shown in FIG. 5a may be used. It is seen to comprise a pair of handles 24 having opposed jaws 25 on one end thereof and where a hinge pin or rivet 28 allows the jaws to open and close relative to one another upon appropriate manipulation of the handles 24. The jaws include a plurality of raised projections, as at 26, that are designed to cooperate with the hooks 27 on the flexible base member of the cuffs 11 to cause them to impinge into the outer urethral wall when the jaws are made to close relative to one another about the tubular organ being addressed.

Figure 8A:
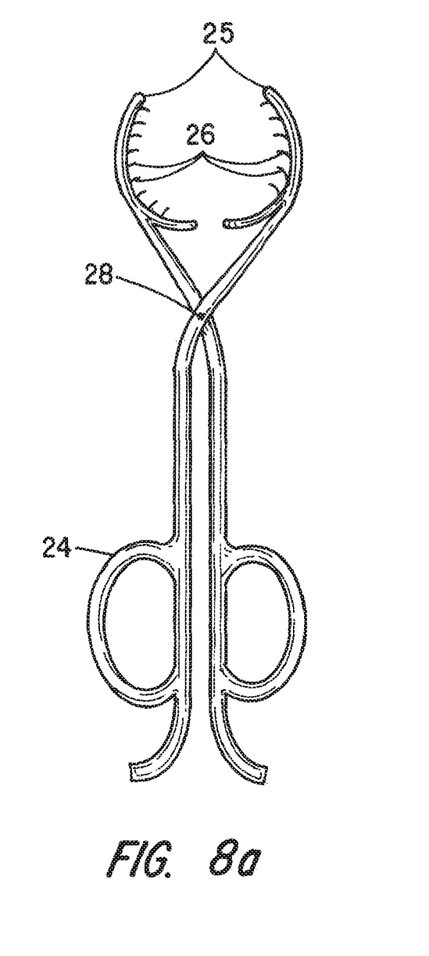
FIGS. 8a through 8e illustrate the manner in which a specially designed tool can be used to secure the cuff of the present invention to the exterior wall of a tubular organ.
Figure 8B:
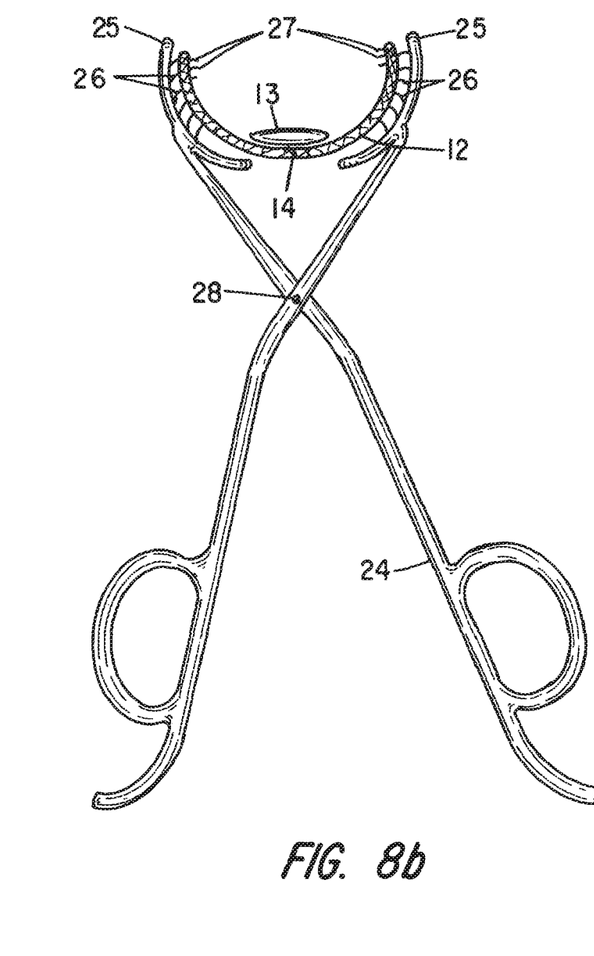
Figures 8C, 8D, 8E:
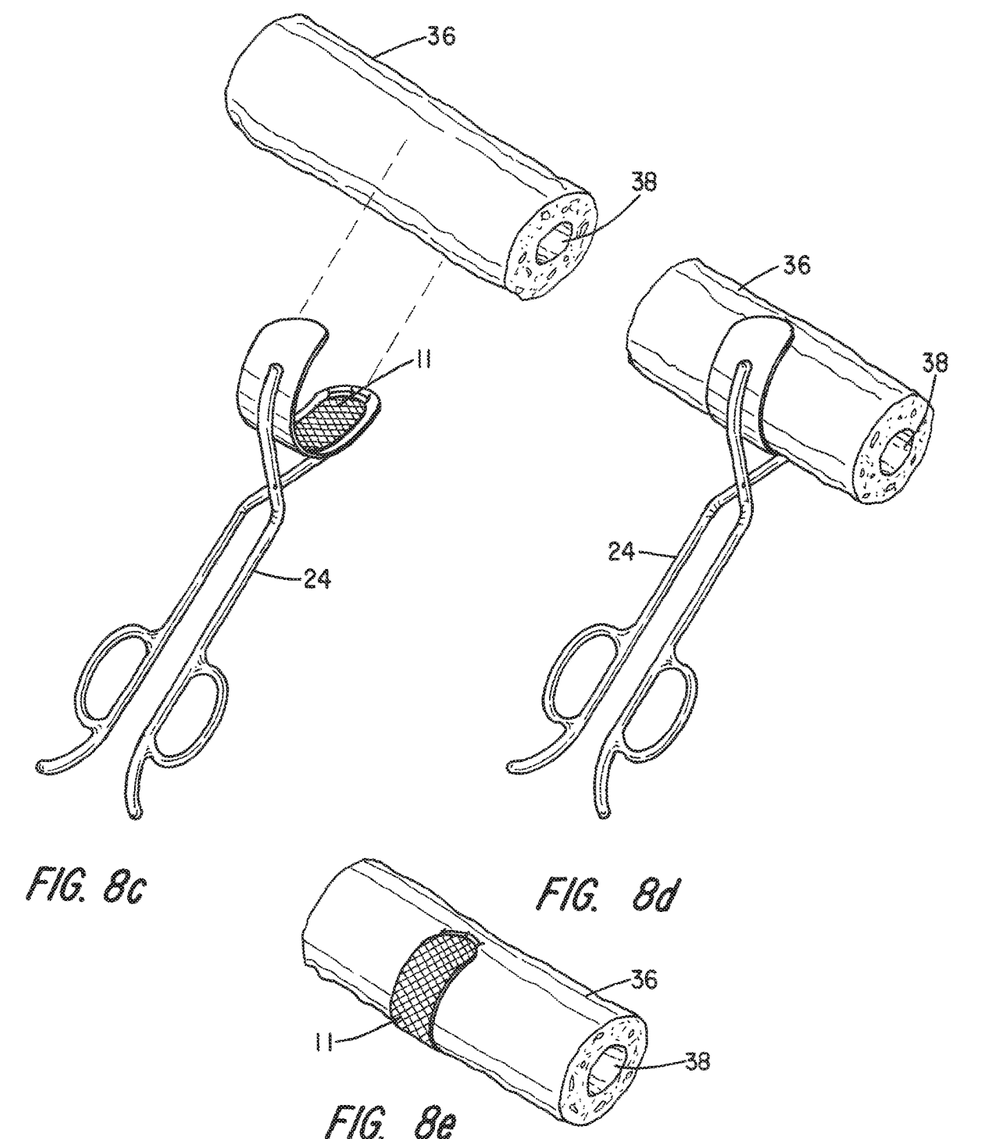

FIG. 5b illustrates the tool of FIG. 5a with a cuff of the present invention positioned between the jaws 25 of the tool just prior to use. The optional expandable component or balloon 13 is centrally disposed. The surgeon will align the index mark or guide line 14 with a length of the urethra as shown in FIG. 5c, and now, when the handles are squeezed together, the jaws 25 will close with the urethra cradled therein. See FIG. 8d. The projections 26 on the tool jaws are designed to cooperate with the hooks 27 on the base member 12 to thereby cause the hooks to pierce into the urethral wall as shown in FIG. 8e and thereby hold the cuff in partially surrounding relation relative to the circumference of the urethra. After a period of time, measured typically in weeks, tissue ingrowth will have occurred, thereby embedding the cuff 11 into the urethral wall and restricting expansion of the urethral wall in the area occupied by the cuff. As earlier described, this increases the flow resistance of the urethra without totally causing occlusion and thereby allowing normal micturition while inhibiting unwanted urine flow from the increases in bladder pressure due to laughing, sneezing, coughing, etc.

In accordance with another aspect of the invention, the cuff may comprise a flexible mesh base member having an expandable component affixed to one major surface of the base member. The cuff will increase the urethral resistance of urine flow by creating a direct and adjustable coaptation in the urethra, but not occluding it. The expandable component is situated on one side of the urethra between the urethral wall and the cuffs base member. As the expandable component inflates, it forces the urethral wall inward as the other side of the expandable member is confined by the cuffs inelastic base member. This results in an inward indentation of the urethral wall, resulting in narrowing of the urethral lumen, leading to an increased coaptation and resistance to urine flow and decreased incontinence.

As the cuff is attached only to the urethra and not to surrounding anatomical structures, the pressure produced by the expandable component will remain the same regardless of the urethral movements. This is a critical, non-obvious difference between the present invention and the traditional urinary bladder support slings. Also, because the cuff is attached only to the urethra, the amount of coaptation can be adjusted, tailoring to the need of the patient's incontinence condition.

In contrast to the Artificial Urinary Sphincter (AUS) previously described, the present invention is a partial cuff. The present invention will not constrain the segment of the urethra opposite the cuff from relaxation and expanding during normal urination, and urine can, therefore, flow naturally past the cuffed region. The patient does not have to actively manipulate a pump mechanism to open the urethral lumen for micturition to occur. Therefore, with the present invention, as opposed to the AUS, patients will be able to micturate normally and naturally without any abnormal manipulation.

Though the invention will be used mostly for women, as incontinence is more pervasive in women, it is also applicable for men's incontinence condition, such as may result in post-prostatectomy situations and in certain post transurethral resection of the prostate situations.

In certain instances, the expandable component on the base member does not need to be expanded, as the act of surgery and its resultant scar formation would provide sufficient compression to the urethra to achieve continence.

A first preferred embodiment of the invention is a cuff that only partially surrounds the urethra or other tubular organ through which flow is to be resisted.

A second preferred embodiment of the invention comprises a cuff composed of a base member and an expandable component on the base member. A portion of the base member can be firmer than the rest of the base member. The partial cuff is adapted to be attached to the urethra with the expandable component facing the urethra.

The expandable component is preferably an inflatable, expansible balloon. The inflation and deflation of the balloon can be done through a port, such as a tube, that can be permanently attached to or detachable from the balloon. The other end of the tube preferably has a self-sealable end for injection or withdrawal of the inflation material during the adjustment of the size of the balloon suitable for the patient's condition. The inflation port may also be a self-sealing patch on the cuff. This patch can be felt through the skin or seen non-invasively via other means for convenient identification by the physician doing the balloon sizing. The self-sealing material of the patch permits piercing by an injection needle without leaking when the needle is removed.

The fixation of the device to the urethra is accomplished by first fastening the base member to the urethral wall and/or biological tissue, followed by tissue ingrowths into the material of the base member over several weeks post surgery.

For example, the base member material is preferably, but not necessarily, a mesh-like synthetic fabric having fringes extending at least beyond the two ends of the balloon and these fringes provide easy stitching or fastening to the urethra by the surgeons and the mesh fabric will allow tissue ingrowths to further naturally and firmly secure the attachment of the cuff to the wall of the involved tubular organ.

The mesh-like fringe can extend along the entire perimeter of the cuff. The fringe area can be substantially larger than the expandable component. A preferred shape of the cuff may be rectangular, but with rounded ends.

The fastening of the cuff to the tubular organ can be accomplished by sutures or by small hook-like elements placed on the cuff or by a suitable adhesive, such as tissue glue, albumin and glutaraldehyde tissue adhesives or polyethylene glycol polymers. The hook-like elements are placed on the same side of the cuff as the expandable component. These hook-like elements fasten the base material to the wall tissue of the anatomical tube, such as the urethral wall tissue, to hold the cuff in place while tissue ingrowths is taking place. Once tissue ingrowths is complete, the cuff becomes integrated into the wall of the tubular organ and these hook elements will no longer be necessary. They can dissolve and be absorbed by the body.

The hook-like elements can be pre-affixed onto the base member of the cuff or applied by the surgeon at the time of implant.

As a further feature, a combination of two types of hook-like elements can be utilized as fasteners. The pre-affixed hook-like elements on the mesh base member serve as a fast general attachment of the cuff and then supplemented by placement of additional hook-like elements to refine the cuff attachment to the tissue. The use of tissue glue or tissue adhesive may also be used to supplement the hook-like elements.

The hook-like elements are preferably made of a biocompatible and bio-resorbable or degradable material known in the art. The hook-like elements eliminate the need for surgeons to suture the cuff to the urethra. With these hooks, the cuff may be applied to the urethra with a simple tool.

For example, a forceps-like tool can be used to apply the cuff to the urethra. Its jaws can be suitably shaped to accommodate the curvature of the tubular organ.

The hooks can be pre-assembled onto the cuff. As already described in connection with FIGS. 8a-8e, two curved forceps jaws, each capturing an end of the cuff, can be used to push the cuff towards and place it against the tubular organ, e.g., the urethra, to partially surround it. Once in place, the handles of the tool are manipulated to set the hooks on the cuff into the wall of the tubular organ from outside in.

The tool embodies a means to hold onto the cuff before deployment of the cuff onto the tissue. Once the cuff is in place and its hooks are embedded into the tissue, the tool can be withdrawn, releasing the cuff and leaving it attached to the tissue.

The means employed to cause the tool's jaws to hold onto the cuff may be small pin-like or hook-like protrusions 26 disposed at an angle on the inside curves of the jaws. These protrusions prevent the cuff 12 from falling off while it is being pushed forward along and against the wall of the tubular organ, as the action of pushing forward forces the cuff to be tightly engaged to the forward pointing protrusions 26. However, after the cuff is fastened onto the tissue wall of the tube, by pulling back the tool, it releases the cuff 12 as these protrusions are now pointing rearward as compared to the movement of the tool jaws. Similarly, but with an opposite intent, the hook-like elements 27 on the cuff will have the hooks pointing rearwards as the cuff is pushed forward by the tool, so that once they are engaged into the tissue, the hook-like elements prevent the cuff from sliding back and off of the tubular organ, e.g. a urethra.

Figure 9:
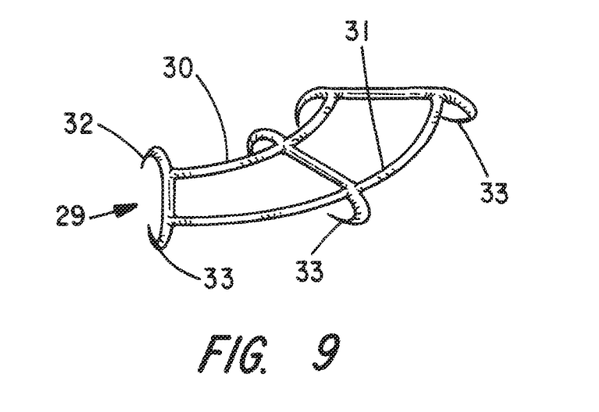
FIG. 9 illustrates an attachment hook assembly.
Figure 10:
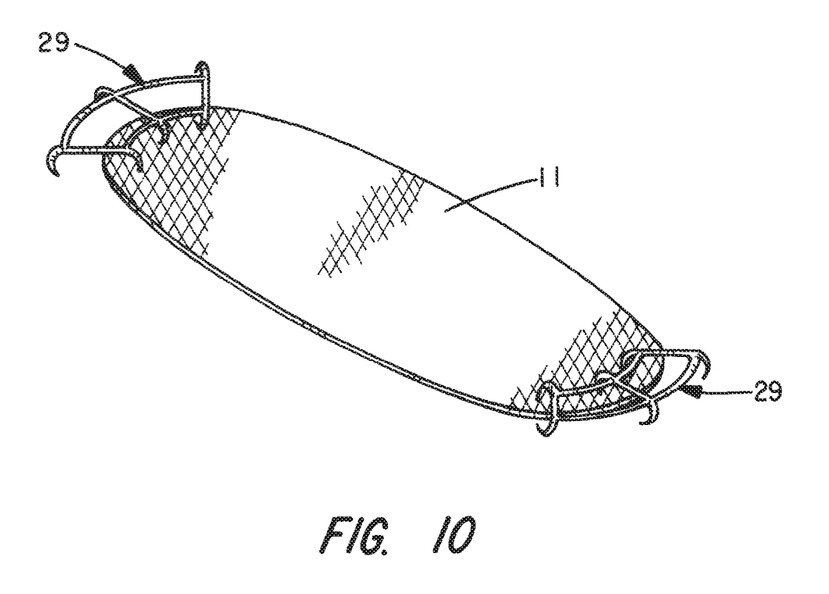
FIG. 10 illustrates the hook assembly of FIG. 9 affixed to a cuff member.

Among different ways of having the hooks preassembled onto the cuff, as in FIG. 3b, an embodiment of a hook assembly like that shown in FIG. 9 may be utilized in a manner illustrated in FIG. 10. FIG. 9 illustrates an example of a hook assembly 29 to be used for attachment of the cuff's base member to the exterior wall surface of a biological tube. The hook assembly may consist of a plurality of hooks 32 that are joined by a pair of connectors 30 and 31 where hooks 32 serve to engage the tissue of the biological tube and the hooks 333 serve to engage the base member 12 of the cuff 11. The connectors 30 and 31 serve to space the hooks in desired locations on the cuff and provide even tension for maintaining the shape of the cuff during attachment to the biological tube. The connectors 30 and 31 can also provide an easy way for reversibly engaging and disengaging the deployment tool. Furthermore, the location of the connector 30 can be situated in a position proximate to the hooks 32 such that it will assist in the deployment handle of the tool pushing down on the hooks 32 in engaging the tissue of the biological tube. Different hook numbers and connectors on the hook assembly can be applied to fit the needs of the particular cuff application. For larger cuffs, one or more of sets of the hooks can be utilized. FIG. 10 illustrates one possible placement of the hook assemblies 29 on the opposed ends of the cuff 11.

The expandable component on the partial cuff can be inflated precisely to achieve the degree of urine flow resistance desired. This is feasible as the adjustment can be carried out a few weeks after the surgery at a time when tissues have healed and inflammation has subsided, therefore allowing more meaningful and accurate adjustment of the urethral coaptation.

As already indicated, the expandable component can be an inflatable balloon with different shape configurations. The expandable component can have different forms, e.g., it could be a single balloon as in FIG. 1, a set of two or more narrow balloons as in FIG. 2, resembling ridges, on the base member. These ridges will preferably be applied to the urethra such that they extend across the urethra, perpendicular to the urine flow pathway. These ridges can also be applied to the urethra such that they are inline with the urethra, parallel to the urine flow pathway creating a longer compression zone. These ridges can also be bilateral on opposite sides of the urethra.

In accordance with a further embodiment, the ridges can also be preformed so that no inflation would be needed. The preformed ridges can be made of silicone rubber or other biocompatible material and there can be open spaces between the pair of ridges.

The material of the base member as well as the inflatable balloon may be made of flexible, biocompatible material, such as silicone rubber. The base member can be made of polypropylene or polyethylene strands or meshes similar to those used in hernia repairs of general surgery and slings of urological surgery.

Additional mechanisms, such as ports and tubes, can be added to make the expandable component of the cuff inflatable and deflatable for future adjustments as the patient's condition changes. The inflation and deflation port can be placed in locations that it can be used in the future without surgery.

Rather than comprising a balloon, the expandable member may comprise a small pouch of moisture permeable material, such as a silicon rubber membrane, micro-porous Teflon membrane or a regenerated cellulose membrane, where the pouch contains a hydrophilic material, such as agarose particles, polyacrylamide particles or serum albumin and that expands on the absorption of moisture.

A midline marking N can be applied to the bottom of the base member to assist the surgeon in aligning the device over the urethra or other tubular organs. Surgically, the cuff can be implanted trans-vaginally, via a single midline incision or a flap at the anterior wall of the vagina in incontinent women patients. To make the surgery easier and as earlier presented, the cuff can be deployed by a deployment tool that holds the cuff for attachment to the outside of the tubular organ and releases the cuff after the cuff is engaged into the tissue.

In a still further alternative embodiment, the cuff may comprise a C-shaped clip formed from a resilient medical-grade plastic or a biocompatible metal rather than a synthetic mesh and that is designed to partially surround a tubular organ, e.g., the urethra.

The clip is designed to span an arc greater than 180° but less than 360° and preferably a range from about 235° to 300° and the effective diameter of which creates somewhat of an interference fit with the tubular organ that is made to surround.

Figure 11:
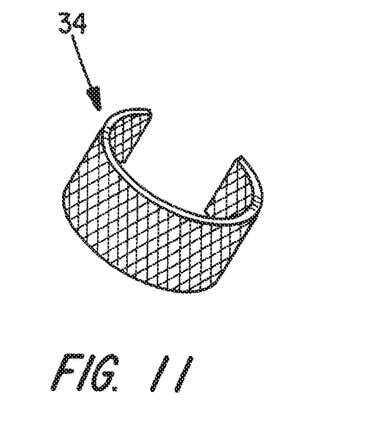
FIG. 11 illustrates a further embodiment of the invention.
Figure 12:
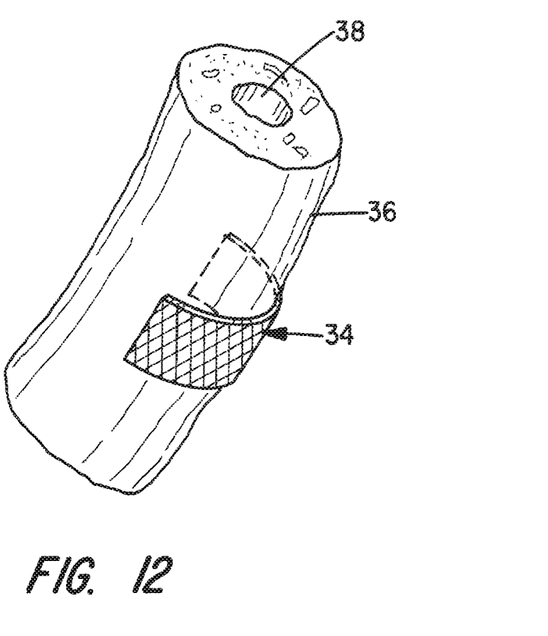
FIG. 12 shows the further embodiment of FIG. 11 affixed to a tubular organ.

Referring to FIG. 11, a first type of C-clip is illustrated and identified by reference numeral 34. FIG. 12 shows the C-clip 34 when clamped onto a tubular organ 36. The presence of the C-clip prevents expansion of the tubular organ 36 subtended by the clip and, in accordance with the present invention, increases the resistance to flow through the lumen 38 of the tubular organ.

While the C-clip shown in FIGS. 11 and 12 comprise a continuous metal or plastic arcuate strip, the clip may also be fenestrated, such as by laser cutting, to facilitate tissue ingrowth therethrough and integration with the vessel wall.

Figure 13:
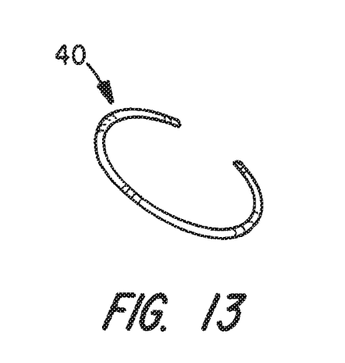
FIG. 13 is yet another alternative embodiment.
Figure 14:
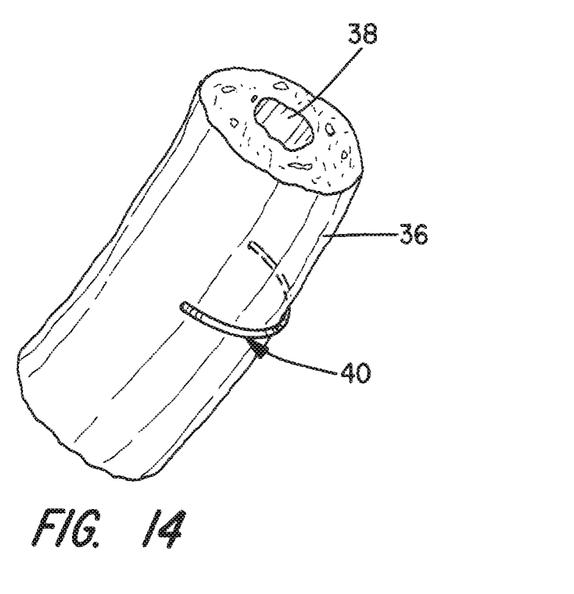
FIG. 14 shows the embodiment of FIG. 13 affixed to a tubular organ.

FIG. 13 shows a C-band 40 comprising a metal or plastic wire or strand that exhibits resiliency, allowing it to be spread for placement about a tubular organ, but when released, closes about the tubular organ as shown in FIG. 14. Rather than simply using a single C-band 40, plural such bands may be placed about the tubular organ in a closely spaced relationship so as to create a desired degree of compression on the tubular organ and, therefore, greater resistance to flow through the lumen 38 thereof. It is also contemplated that one or more C-bands 40 can be applied over a soft, partial mesh cuff like that shown in FIG. 1b to hold it in place on the tubular organ while tissue ingrowth occurs. When so used, the C-bands can be made of bioresorbable or biodegradable material.

Figure 15:
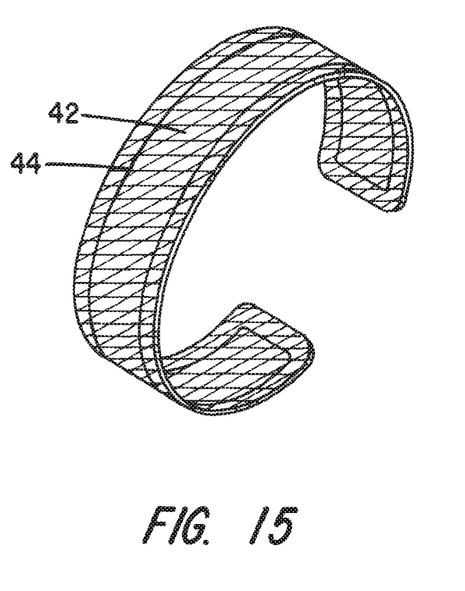
FIG. 15 shows a mesh material affixed to a C-shaped wire frame.

FIG. 15 shows yet another way of implementing the partial banding of a fluid carrying tubular organ to increase its resistance to flow. Here, a polypropylene mesh strip 42 is supported by a frame member 44 formed from a suitable metal or plastic exhibiting a memory property when stressed below its elastic limit and then released. Without limitation, the frame may comprise a nitinol wire that has been heat treated in a mold to form the C-shape configuration illustrated in FIG. 15. When the band is spread, placed about a tubular organ and then released, the mesh strip is brought into intimate engagement with the tubular organ and over a few-week period becomes endothelialized, thus reinforcing the organ wall at the placement site.

The cuff is suitable for treating females with stress incontinence. The cuff is also suitable for men with incontinence, such as may occur after radical prostatectomy, other procedures or in conditions where an increased resistance to urine flow would be beneficial in controlling incontinence.

The cuff of the present invention may find other uses. It can be suitable to treat ureteral reflux or to minimize food regurgitation or reflux into the esophagus, limit the food intake into the stomach, and strengthen the ventricular wall of the hypertrophied heart and blood vessels. It is also contemplated that the partial cuff of the present invention can be used to minimize fecal incontinence. In fact, the partial cuff may be suitable for treating conditions where material is passed in an anatomical tube in which the flow of material needs to be modulated.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. An apparatus comprising:
   a curved shape-memory material extending from a first end to a second end, the first end and the second end curving toward one another and defining a gap between the respective first and second ends when the curved shape-memory material is in a relaxed state; and
   a surface material extending along an inner curved surface of the shape-memory material and configured and arranged to facilitate tissue in-growth, the shape-memory material being configured and arranged with the surface material to:
      in response to the shape-memory material being expanded and subsequently released onto an outer surface of tubular tissue having a radius of curvature that corresponds to a radius of curvature of the shape-memory material in the relaxed state, engage the surface material onto the outer surface of the tubular tissue with the inner curved surface extending in a tubular shape along a length of the outer surface of the tubular tissue; and
      via the engaging, restrict fluid flow through the tubular tissue along the length of the inner curved surface by applying pressure for restricting expansion of the tubular tissue, via engagement of the surface material along the length of the outer surface of the tubular tissue.

2. The apparatus of claim 1, wherein the shape-memory material and surface material are configured and arranged to constrain expansion of the outer surface of the tubular tissue along an entire surface area of the outer surface thereof that is in contact with the apparatus.

3. The apparatus of claim 1, comprising a base structure that includes the shape-memory material and the surface material, the base structure having a radius of curvature that is defined by the radius of curvature of the shape-memory material, the base structure being configured and arranged to constrain the outer surface of the tubular tissue in contact with the base structure.

4. The apparatus of claim 1, wherein the shape-memory material is configured and arranged to, when in use with the tubular tissue, constrain the tubular tissue with the first and second ends partially surrounding a circumferential surface area of the tubular tissue and the gap between the first and second ends leaving a remaining portion of the circumferential surface area uncompressed.

5. The apparatus of claim 4, wherein the first and second ends extend, when in use with the tubular tissue, along an arc around the tubular tissue that is at least half way around the circumferential surface area.

6. The apparatus of claim 1, wherein the first and second ends extend, when in use with the tubular tissue, along an arc around the tubular tissue that is at least half way around a circumferential surface area of the tubular tissue.

7. The apparatus of claim 1, wherein the shape-memory material is configured and arranged to, in response to being expanded to increase distance between the first and second ends across the gap and subsequently released around the outer surface of the tubular tissue, constrain the surface material and the inner curved surface onto the outer surface of the tubular tissue, by returning toward the relaxed state and resting in a partially-expanded state in which the distance between the first and second ends across the gap is greater than the distance between the first and second ends across the gap when the shape-memory material is in the relaxed state.

8. The apparatus of claim 1, wherein the shape-memory material is configured and arranged to constrict all surface areas of the tubular tissue with which the apparatus is placed in contact.

9. The apparatus of claim 1, wherein the shape-memory material is configured and arranged to restrict expansion of the tubular tissue for restricting fluid flow therein, using force solely applied by the shape-memory material.

10. The apparatus of claim 1, wherein the shape-memory material is configured and arranged to constrain the outer surface of the tubular tissue in response to fluid flow therein by restricting expansion of the tubular tissue and therein restricting the fluid flow therein with the first and second ends terminated on the tubular tissue, by utilizing the shape-memory material tissue in-growth via the surface material to impart structural rigidity between the first and second ends sufficient to passively limit flow of material through a lumen of the tubular tissue.

11. The apparatus of claim 1, wherein the shape-memory material is configured and arranged to restrict the fluid flow through the tubular tissue by restricting expansion of the tubular tissue, prior to tissue in-growth from the tubular tissue to the surface material.

12. The apparatus of claim 1, wherein the shape-memory material is configured and arranged to decrease elasticity of the tubular tissue predominantly via structural rigidity of a portion of the shape-memory material that extends between the first and second ends and into which the tissue is grown.

13. The apparatus of claim 12, wherein the shape-memory material is configured and arranged to decrease the elasticity of the tubular tissue without interaction between the apparatus and any other tissue in a patient in which the tubular tissue resides.

14. The apparatus of claim 1, wherein the shape-memory material is configured and arranged to exhibit, upon engaging with the tubular tissue, an internal structural rigidity that restricts expansion of muscle in an outer wall of the tubular tissue, thereby increasing a force required to open the tubular tissue while allowing the tubular tissue to move independently from other tissue in a patient in which the tubular tissue resides.

15. The apparatus of claim 1, wherein the surface material is fenestrated.

16. A method comprising:
expanding a curved shape-memory material that extends from a first end to a second end, the first end and the second end curving toward one another and defining a gap between the respective first and second ends when the curved shape-memory material is in a relaxed state, so that the distance between first and second ends across the gap is larger than said distance in the relaxed state;
providing a surface material extending along an inner curved surface of the shape-memory material, the surface material being configured and arranged to facilitate tissue in-growth; and
releasing the expanded shape-memory material onto an outer surface of tubular tissue having a radius of curvature that corresponds to a radius of curvature of the shape-memory material in the relaxed state, and therein engaging the surface material with the outer surface of the tubular tissue and, via the engaging, restricting fluid flow through the tubular tissue.

17. The method of claim 16, wherein restricting the fluid flow includes constraining expansion of a cylindrical outer surface of the tubular tissue along a length of an entire cylindrical surface area of the outer surface thereof that is in contact with the surface material.

18. The method of claim 16, wherein restricting the fluid flow includes constraining the tubular tissue with the first and second ends partially surrounding a circumferential surface area of the tubular tissue and the gap between the first and second ends leaving a remaining portion of the circumferential surface area-unconstrained.

19. The method of claim 16, wherein restricting the fluid flow includes by compressing an inner surface of the entire surface material and curved shape-memory material onto the outer surface of the tubular tissue, using stiffness of the shape-memory material and the tubular tissue to maintain the shape-memory material in a partially expanded state and by restricting expansion of the tubular tissue.

20. The method of claim 16, wherein providing the surface material includes providing a fenestrated surface material.

* * * * *